United States Patent [19]

Bodie et al.

[11] Patent Number: 5,437,992
[45] Date of Patent: Aug. 1, 1995

[54] FIVE THERMOSTABLE XYLANASES FROM MICROTETRASPORA FLEXUOSA FOR USE IN DELIGNIFICATION AND/OR BLEACHING OF PULP

[75] Inventors: Elizabeth A. Bodie, Belmont; William A. Cuevas, San Francisco, both of Calif.; Marja Koljonen, Kauniainen, Finland

[73] Assignee: Genencor International, Inc., Rochester, N.Y.

[21] Appl. No.: 234,338

[22] Filed: Apr. 28, 1994

[51] Int. Cl.$^6$ .................. C12N 9/24; C12N 1/12; D21C 3/00; C07G 17/00
[52] U.S. Cl. .................. 435/200; 435/278; 435/252.1; 435/822; 536/124
[58] Field of Search .............. 435/200, 252.1, 822, 435/278; 536/124

[56] References Cited

FOREIGN PATENT DOCUMENTS

0473545a2 3/1992 European Pat. Off. .
602597 6/1994 European Pat. Off. .
WO92/18612 10/1992 WIPO .

OTHER PUBLICATIONS

Naruse et al., J. of Antibiotics, 46(12), 1804–1811, 1993.
Speth et al., Biol. Chem. Hoppe-Seyler, vol. 370, 591–9, 1989.
Chenglin et al., Acta Microbiol. Sin., 29(1), 7–14, 1989.
Miyadoh et al., Int'l. J. of Syst. Bacteriol., 39(2), 152–158, 1989.
Toda et al., J. of Antibiot., 46(6), 875–883, 1993.
Athalye et al., J. of General Microbiol., 130, 817–23, 1984.
Ghangas, et al., "Cloning of a *Thermomonospora fusca* Xylanase Gene and Its Expression in *Escherichia coli* and *Streptomyces lividans*", *J. Bacteriology,* 171(6):2963–2969 (Jun. 1989).
Holtz, et al., "Production and properties os xylanases from thermophilic actinomycete", *Antonie van Leeuwenhoek,* 59:1–7 (1991).

*Primary Examiner*—David M. Naff
*Assistant Examiner*—Mike Meller

[57] ABSTRACT

Five xylanases are purified from the microorganism, *Microtetraspora flexuosa*,preferably strain ATCC 35864. Each biochemically unique xylanase is thermostable and has optimal activity in alkaline conditions. These enzymes are excellent candidates for enhancing the delignification and bleaching of pulp. Furthermore, treating the pulp with the above enzymes prior to bleaching may reduce the amount of chlorine containing and/or peroxide chemicals required in the bleaching process.

11 Claims, 3 Drawing Sheets

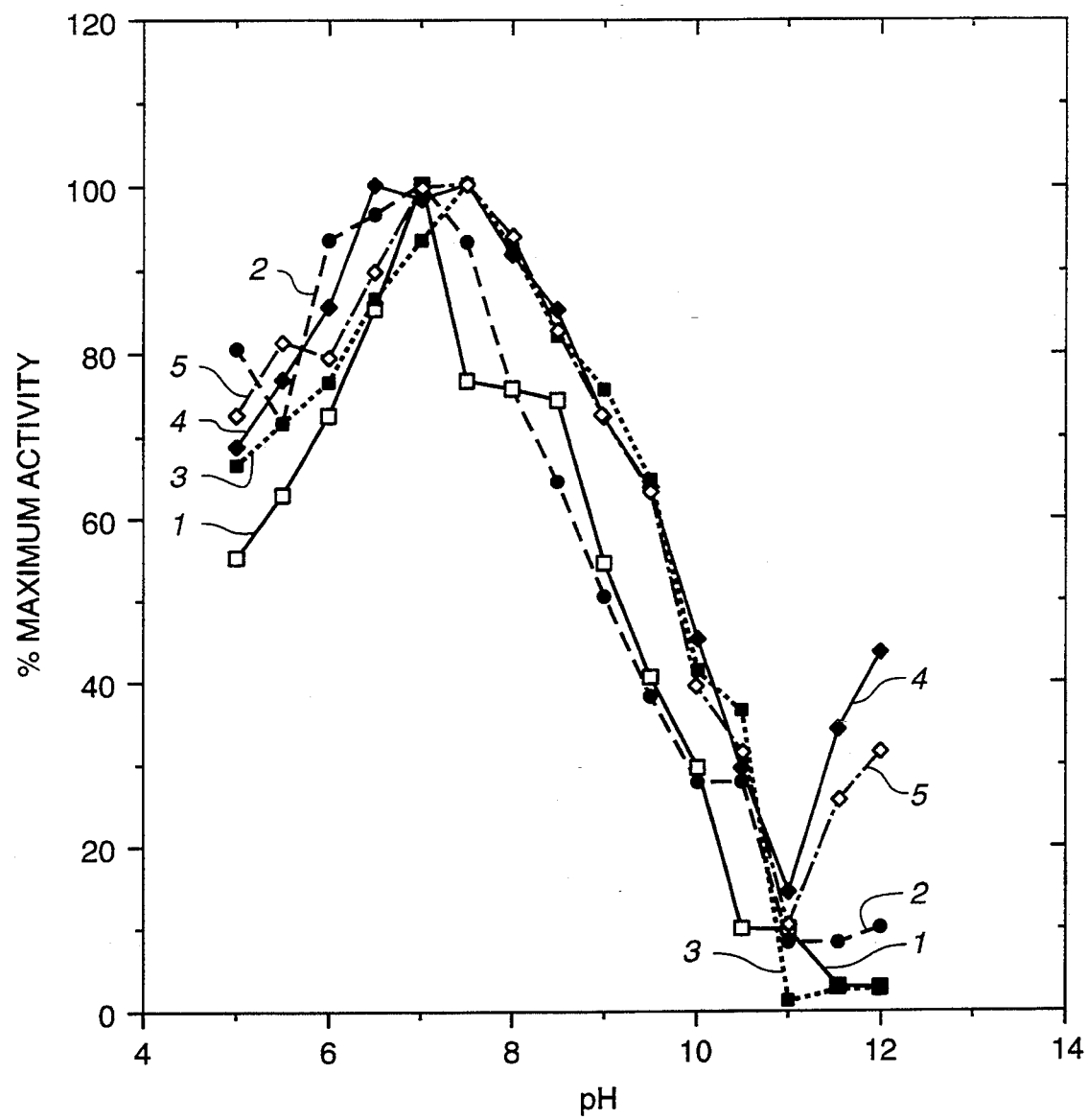
FIG._1

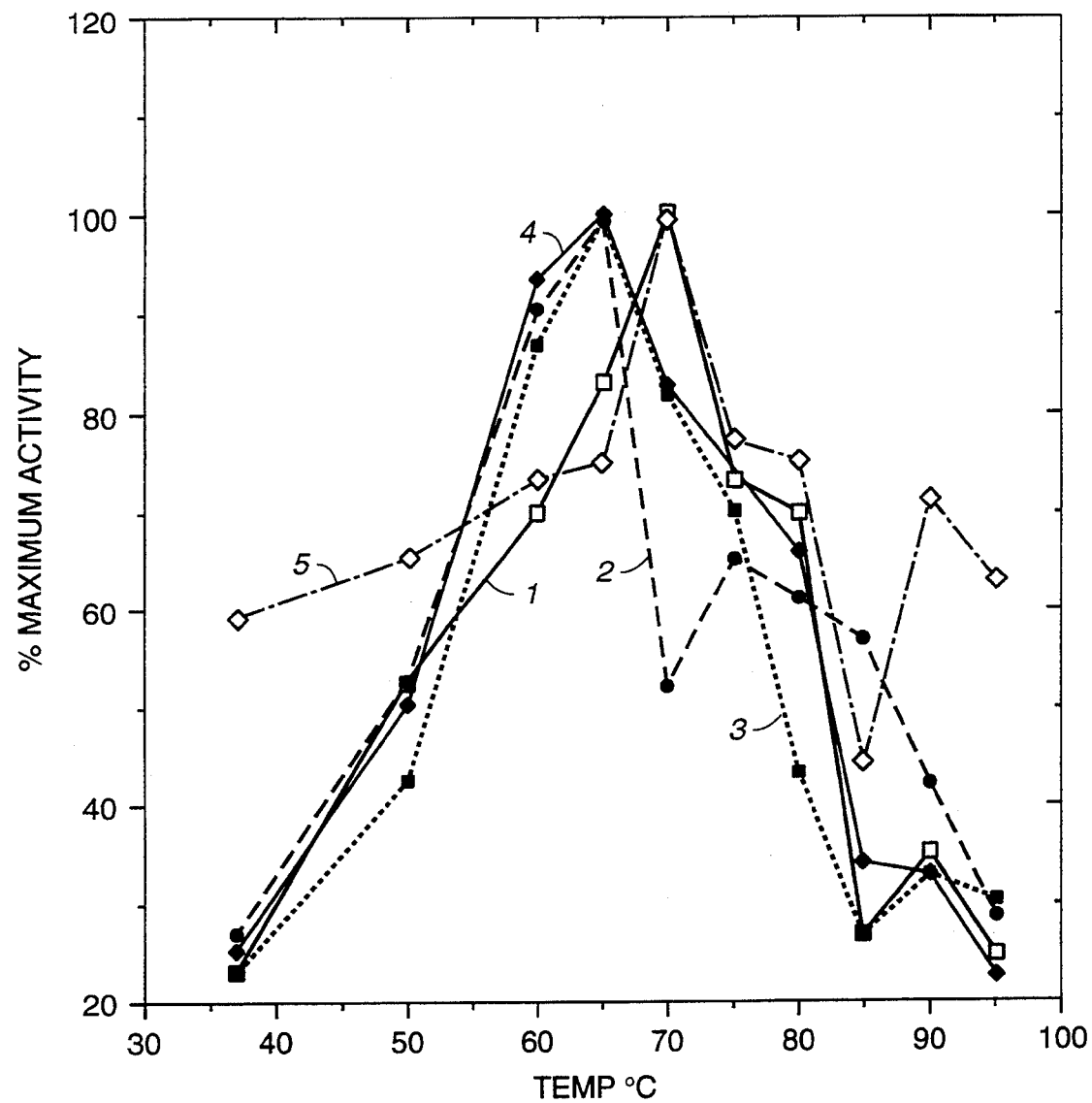
FIG._2

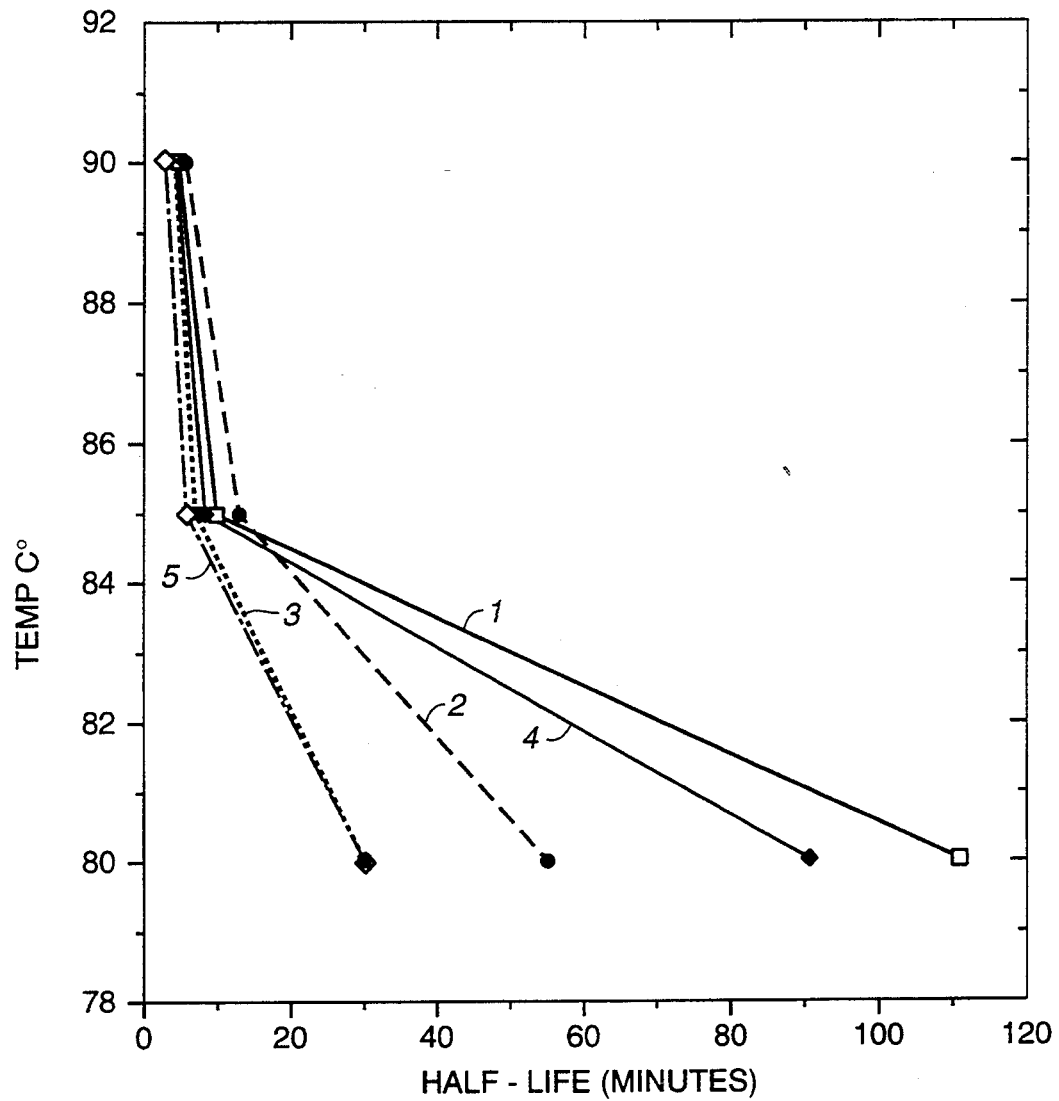
FIG._3

FIVE THERMOSTABLE XYLANASES FROM MICROTETRASPORA FLEXUOSA FOR USE IN DELIGNIFICATION AND/OR BLEACHING OF PULP

FIELD OF THE INVENTION

The present invention relates to methods utilizing thermostable enzymes obtained from *Microtetraspora flexuosa* strains and novel *Microtetraspora flexuosa* thermostable xylanase enzymes that are active over a wide alkaline range and high temperatures. Alkaline thermostable xylanases have particular application in the pulp and paper industry.

BACKGROUND OF THE INVENTION

Wood is a complex material which is composed of cellulose, hemicellulose and lignin along with other minor components. Lignin is associated with cellulose and hemicellulose, and is probably covalently bound to both cellulose and hemicellulose.

In the paper-making process, lignin is generally removed from the wood pulp since it lends a brownish color, reduces strength and imparts other undesirable characteristics to the finished product. Removal of lignin can be achieved in many ways.

A majority of the lignin is initially removed from wood pulp through chemical pulping (e.g. kraft process). In the subsequent bleaching process, chemical pulp is routinely reacted with chlorine and other delignifying chemicals to further remove lignin and then reacted with bleaching agents to modify the lignin from pulp, providing a stable brightened pulp. However, the treatment with chlorine is undesirable from an environmental standpoint because the resulting effluents contain a large number of toxic compounds (e.g. chlorinated phenolics). Concern about the environmental harmful effects caused by pulp bleaching with chlorine containing chemicals has driven the industry to seek alternative bleaching methods.

Attempts to use enzymes derived from fungal and bacterial sources to enhance delignification and brightening, while lowering or eliminating the use of chlorine chemicals have been described in the literature. However, very few enzyme systems have been found which selectively act on pulp but do not adversely affect the cellulosic content of pulp.

Xylanases are hemicellulase enzymes that catalyze the hydrolysis of xylan, a major component of hardwood and softwood hemicellulose, and are usually associated with the cellulose and lignin components of plant cell walls. Xylanase has proven to be a valuable enzyme for the pre-bleaching of pulp to enhance delignification of wood pulp by facilitating the removal of lignin from pulp. A proposed mechanism for this action is that during kraft pulping, xylan is first solubilized in the cooking liquor. In the later stages of the cook xylan is reprecipitated on the pulp fibres. When xylanases are used in the pre-bleaching of pulp, partial hydrolysis of these reprecipitated xylan fractions renders the pulp surface more permeable for lignin removal. Therefore, xylanase pre-bleaching results in the use of lower amounts of bleaching chemicals as compared to nonenzymatic bleaching. Most of the enzyme preparations initially described in the literature are active at acidic pH ranges with optimal temperatures reaching 50° C.

For industrial application, especially in the pulp bleaching industry where the processes take place at high temperatures and alkaline pH, it would be significantly advantageous if xylanases were available which are active at high temperatures over a wider pH-range, especially pH 7-10, than are now currently available.

The xylanases purified from *Microtetraspora flexuosa* are excellent candidates in the pre-bleaching of pulp because they are active at high temperatures and alkaline pH, and they act on the hemicellulose/cellulose matrix of the pulp with which the lignin is associated or bound, such that after enzyme treatment, the lignin is released and/or rendered releasable by an appropriate extractant.

Recently, several thermophilic xylanases from fungal and bacterial microorganisms have been identified. For example, a thermophilic xylanase has been isolated from Actinomadura reclassified as Microtetraspora having an optimal pH of 6.0-7.0 and temperature range of 70° to 80° C. (Holtz, C. et al Antonie van Leewenhoek 59:1-7, 1991). EP 0473545 discloses that the bacterial strain *Thermomonospora fusca* produces thermostable xylanases active at temperatures 10°-90° C., preferably, 50°-80° C. over a wide pH range, i.e., from about 5-10, with the more preferred range between 6.6-9.5. In addition, WO92/18612 discloses a xylanase enzyme derived from the genus, Dictyoglomus, having activity over a broad pH range (5.0-9.0) and thermostability at temperatures ranging from 60° to 90° C.

Although thermostable xylanases active in the alkaline range have been described in the literature, the need still exists to identify novel xylanases that are more efficient in applications relating to delignifying and brightening of pulp compared to conventional bleaching agents and xylanases now available. Moreover, at the time of Applicants' invention, multiple xylanases from *Microtetraspora flexuosa* were unknown to exist that have optimal xylanase activity in the alkaline range.

SUMMARY OF THE INVENTION

In accordance with the present invention, five novel alkaline, thermostable xylanases from microorganisms Microtetraspora flexuosa have been isolated which may withstand high temperatures and alkaline conditions. This is of particular relevance in pulp bleaching applications. It has also been found that whole culture broth supernatant of *Microtetraspora flexuosa* microorganisms have thermotolerant and alkaline tolerant characteristics that make these xylanase mixtures excellent candidates in pulp bleaching applications. These novel xylanase and whole culture supernatant xylanases may also find application in other areas, such as animal feed and fuel industries.

In accordance with one aspect of the present invention, five novel xylanase enzymes isolated from *Microtetraspora flexuosa*, named herein xylanase 1 through xylanase 5, have been purified to homogeneity as measured by silver staining isoelectric focusing gels. The xylanases have been purified by a combination of ion-exchange chromatography and hydrophobic interaction chromatography. Each purified xylanase is characterized as being thermostable over a wide pH range. Specifically, each xylanase retains greater than 80% activity in the pH range of 6-9.

The xylanases may be further characterized as follows: xylanase 1 has an apparent molecular mass of about 33,100 daltons, pI of about 8.5, an optimum pH of about 7.0-7.5, and exhibits an optimum temperature activity of about 70° C. Xylanase 2 has an apparent molecular mass of about 13,300 daltons, pI of about 7.5, an optimum pH of about 7.0–7.5 and exhibits an optimum temperature activity of about 65° C. Xylanase 3 has an apparent molecular mass of about 31,000 daltons, pI of about 6.2, an optimum pH of about 7.5 and exhibits an optimum temperature activity of about 65° C. Xylanase 4 has an apparent molecular mass of about 50,000 daltons, pI of about 5.8, an optimum pH of about 7.5 and exhibits an optimum temperature activity of about 65° C. Xylanase 5 has an apparent molecular weight of about 35,000 daltons, pI of about 5.3, an optimum pH of about 7.5 and exhibits an optimum temperature activity of about 70° C.

The *Microtetraspora flexuosa* xylanases described above may be selectively applied to a variety of pulps at increased temperature and alkaline conditions, whereby the delignification is enhanced, lignin content is reduced, the brightening effect is enhanced, and the cellulosic content of the pulp remains unaffected. Therefore, in accordance with the second aspect of the present invention, one or more of the above described novel xylanase enzymes is applied to treat chemical pulp after digestion or after oxygen delignification to enhance brightening and/or enhance delignification of the treated pulp.

In yet another aspect, the present invention is directed to the application of natural crude whole supernatant xylanases produced in the *Microtetraspora flexuosa* culture broth to enhance delignification and bleaching of the treated pulp. In this aspect, the whole supernatant of *Microtetraspora flexuosa* is a mixture of all the xylanases, namely 1 through 5, produced by *Microtetraspora flexuosa*. The whole xylanase supernatant is thermostable and alkaline stable. The characteristics of the whole xylanase supernatant are as follows: The xylanase activity has a broad pH optimum of 7 to 9, a temperature optimum of about 70° C. to about 80° C. (with 40% of the activity retained at 90° C.), and a half-life at 80° C. for 90 minutes.

BRIEF DESCRIPTION OF THE DRAWINGS

FIG. 1 depicts the activity pH profile of the five purified xylanases from *Microtetraspora flexuosa*.

FIG. 2 depicts the activity temperature profile of the five purified xylanases from *Microtetraspora flexuosa*.

FIG. 3 shows the temperature stability profile of the five purified xylanases from *Microtetraspora flexuosa*.

DETAILED DESCRIPTION OF THE INVENTION

As noted above, the present invention generally relates to novel xylanases produced and isolated from the strain *Microtetraspora flexuosa* as well as methods employing these novel xylanases. When applied at the appropriate pH, temperature and dosage conditions, these unique xylanases from *Microtetraspora flexuosa* are particularly effective in enhancing brightening and delignifying pulp, without adversely affecting the quality of the pulp. These novel xylanases are also excellent candidates for application in animal feed, and as additives to agricultural waste for the production of alcohol fuels.

Prior to discussing this invention in detail, the following terms will first be defined.

As used herein, the term "xylanase number" refers to one of the five purified xylanase enzymes isolated from Microtetraspora ssp culture broth. The numbers assigned to each of the five xylanase correspond to the isoelectric focusing (pI) values of each xylanase, with the lowest number (1) representing the most alkaline pI value and the highest number (5) representing the least alkaline pI value.

The term "whole supernatant xylanases" refers to the culture broth of Microtetraspora ssp. in which the cells have been previously removed by centrifugation. Thus, the whole xylanase supernatant contains a mixture of xylanases 1 through 5 as described above. The term "bleaching" refers to the treatment of chemical pulps and may be evidenced by delignification and brightening of the pulp. The particular applicable pulps will generally already have approximately 90 to 99% of their lignin removed and are treated essentially to remove residual lignin including chemical modified lignin.

In accordance with the present invention, five novel xylanases produced in cultures of *Microtetraspora flexuosa* have been isolated to apparent homogeneity and biochemically characterized. The xylanases of the present invention may be derived from any Microtetraspora ssp that is known in the art. Preferably, the xylanases are derived from Microtetraspora flexuosa. A preferred strain is ATCC 35864 which is readily available from the American Type Culture Collection, Bethesda, MD. The isolation of the novel xylanases involves the purification of the extracellular xylanases by a combination of ion exchange chromatography (IEC) and hydrophobic interaction chromatography (HIC) in either order depending on the xylanase that is purified. Five xylanases were isolated from Microtetraspora and designated as numbers 1 through 5 which correspond to the isoelectric focusing point of each xylanase, with xylanase 1 being the most alkaline and xylanase 5 being the least alkaline.

The two purification methods used to isolate and characterize the five chemically distinct xylanases are detailed below. In both methods, *Microtetraspora flexuosa* cells are removed by centrifugation and the culture broth is concentrated using ultrafiltration. In the first method, xylanase 1 (pI 8.5), xylanase 2 (pI 7.5), and xylanase 4 (pI 5.8) are separated and purified. The cell free whole culture broth preparation is applied to an anion-exchange column, washed and eluted with an increasing salt (NaCl) gradient. After the fractions are collected, xylanase activity is measured using a remazol brilliant blue dyed brichwood xylan assay (RBB-xylan assay). Xylanase 1 and xylanase 2 elute in the column breakthrough. The effluent breakthrough is pooled and reloaded onto a hydrophobic interaction column (phenyl Sepharose). Xylanase 1 and xylanase 2 separate from each other by eluting the column with increasing concentrations of ethylene glycol. Xylanase 4 binds to the anion exchange column and elutes in the salt gradient with the other bound xylanses (xylanases 3 and 5). Xylanase 4 was separated from the other xylanases by HIC (See Example 4 for further detail). Purified xylanases 1, 2 and 4 were further analyzed by isoelectric focusing and mass spectrophotometry (MS) or sodium dodecyl sulfate polyacrylamide gel electrophoresis (SDS-PAGE).

In the second method, the cell free whole culture broth described above was subjected to HIC as a first step to purify xylanase 3 (pI 6.2) and xylanase 5 (pI 5.3). Both xylanases co-elute at the same concentration of ammonium sulfate. To separated xylanase 3 and xylanase 5 from each other, IEC was performed on the pooled eluted active enzyme material. Xylanase 3 elutes from an anion-exchange column at a lower salt concentration than xylanase 5. Both purified xylanases were further characterized by isoelectric focusing and MS or SDS-PAGE.

Each xylanase has been distinguished from each other by its unique biochemical characteristics, eg., molecular weight, pI, optimum temperature and pH, hydrophobic properties and temperature stability. All five xylanases can tolerate high temperatures (ranging from 70° to 90° C.) and alkaline conditions (ranging from about pH 7.0 to 10.0). The five purified xylanases have a half life at 80° C. ranging from 35 minutes to 110 minutes (FIG. 3). A further characterization of each of the five xylanases purified to homogeneity is described in Example 5.

In another embodiment, the xylanases of the present invention have applications in enhancing the delignification and/or the bleaching of pulp. The process comprises contacting the pulp with whole supernatant xylanase, or one or more of the above described purified xylanases and is dependent upon factors such as pH, temperature, treatment time, dosage of enzyme and the quantity and type of pulp.

It is preferred that the above process be carried out at a temperature and pH which will enhance the enzymatic activity. Temperatures may range from approximately 50°–90° C., with 70°–85° C. being preferred. The preferred pH for the process ranges from about 6–10, preferably from about 7 to about 9, most preferred above 7 to about 9. It is characteristic for the purified xylanases of the present invention to be active over a wide alkaline pH-range as well as having high activity at the preferred pH range of about 7 to about 9.

The preferred treatment period for applying the purified xylanases of the present invention is from about 30 minutes to about 4 hours depending upon factors such as the results desired, the quantity and quality of pulp treated and concentration of enzyme, for example.

A suitable enzyme dosing is about 0.10 to 200 units/g of dry pulp more preferably 0.50 to 50 units/g. The xylanase activity of the enzyme preparations is determined as follows: To 1.8 ml of xylan solution (0.6% Sigma No. X-0627, prepared in 0.05 m sodium acetate buffer and adjusted to pH 5.3 with acetic acid), 0.200 ml of suitably diluted enzyme in the same buffer is added. The solution is incubated at 40° C. for exactly 30 minutes. The reaction is then stopped by adding 3 ml DNS reagent (3,5-dinitrosalicylate 10 g/l; Na,K tartrate 300 g/l), and the color is developed by boiling the sample for 5 minutes. The absorbency is then measured at a wave length of 540 nm. One enzyme unit liberates one micromole of reducing sugars calculated at xylose per minute under assay conditions. The activity is calculated from an enzyme dilution liberating 4 micromoles of reducing sugar under assay conditions.

The present invention may be applied to upgrade or assist in the upgrading of any of a wide variety of processed pulps, i.e., pulps which have been already previously treated in any of a variety of ways to reduce their lignin content and are treated in the process according to the invention to further enhance the lignin removal by chemical methods. The present invention may be applied to treat hardwood and softwood kraft pulps to enhance lignin removal and brightening of the pulps. The invention is particularly applicable to chemical pulps, i.e., those in which the lignin component has been chemically modified by various chemical treatments such as in the sulfate (kraft) processes and oxygen delignification, and is preferably applied to kraft pulps. In a preferred method, the enzymes of the present invention are applied to the pulp after kraft digestion or oxygen delignification but prior to bleaching. In the case where both kraft digestion and oxygen delignification are performed on the same pulp, the enzyme is applied after kraft digestion, prior to oxygen delignification or after oxygen delignification. The present invention is also applicable to ozone bleached pulps.

The resulting pulp is treated to remove the releasable lignin component using an appropriate extractant. In another embodiment, pulp treated with the enzymes of the present invention may be subsequently treated with lignin-degrading chemicals such as chlorine, chlorine dioxide and peroxide, and further extracted with an appropriate extractant. In yet another embodiment, the enzyme treated pulp may be treated with an appropriate extractant, followed by lignin degradation and a final treatment with an appropriate extractant. Such extractants essentially solubilize the affected lignin component and suitable extractants include but are not limited to bases such as alkali metal hydroxides (E), DMF, dioxane, acetone, and alcohol. Hydroxide extractions may be combined with hydrogen peroxide ($E_p$) or oxygen ($E_o$). The resulting pulp may then be further bleached by a chemical bleaching sequence such as chlorine dioxide (DED) or peroxide (P-P) to the desired brightness whereby substantial savings of chemicals are observed when compared to pulp bleached to the same brightness by the same sequence but without using the enzyme treatment. Reduction of chlorine containing chemicals or peroxide is achieved in such a way. In addition, by performing the present invention with the above presented enzymes, one may apply the same amount of bleaching chemicals to the pulp and yet achieve a greater brightness in the treated pulp.

In another embodiment, the present invention provides for additional applications of the purified enzymes described above or whole xylanase supernatant from Microtetraspora ssp. in a variety of industrial settings. Specifically, the purified xylanases or whole xylanase supernatant produced in Microtetraspora ssp and described hereinabove may be used to (1) enzymatically breakdown agricultural wastes for production of alcohol fuels and other important industrial chemicals or (2) enzymatically modify animal feeds or feed components or be added to animal feeds for in vivo breakdown of the hemicellulose fraction.

In order to further illustrate the present invention and advantages thereof, the following specific examples are given, it being understood that the same are intended only as illustrative and not limitative.

EXAMPLE 1

Enzyme treatment of oxygen delignified softwood kraft pulp prior to D-E-D bleaching Oxygen delignified softwood kraft pulp, kappa number 16.4 was treated with whole supernatant xylanases derived from *Microtetraspora flexuosa* under the following conditions:

| Enzyme dosage | 5 DNS U/g pulp d.s. |
|---|---|
| pH | 7.5 8, 9 or 10 |
| Temperature | 70° C., 80° C. or 90° C. |
| Reaction time | 2 hours |
| Pulp consistency | 10% |

Before adding the enzyme solution into the pulp mixture, the pH of the pulp was adjusted to the value desired with sulfuric acid and the pulp mixture was preheated in a microwave oven to reach the reaction temperature required. After pH adjustment and preheating the pulp mixture, the enzyme was thoroughly mixed into the pulp mixture and kept 2 hours in a waterbath at the temperature desired.

After enzyme treatment, the pulp mixture was filtered in a Buchner funnel and the pulp was washed with water.

The reference pulps were treated in each pH/temperature combination as described above without adding any enzyme.

Chemical bleaching

After the enzyme or reference treatment, the pulp samples were chemically bleached using the bleaching sequence D-E-D. In both D (chlorine dioxide) stages 100% chlorine dioxide was used.

The reaction conditions in the chemical bleaching were as follows:

TABLE 1

| Bleaching stage | Reagent % of pulp d.s. | Reaction Conditions | | |
|---|---|---|---|---|
| | | T, C | t, min | Cons., % |
| D | 2.6 (act. $Cl_2$) | 55 | 45 | 3 |
| E | 1.5 (NaOH) | 60 | 90 | 10 |
| D | 2.0 (act. $Cl_2$) | 70 | 180 | 10 |

After chemical bleaching the pulp samples were acidified with $SO_2$ water to a pH value of 3.5 at room temperature.

The bleached pulps were analyzed for brightness (ISO) according to SCAN-C11:75. The delignification was measured as change in kappa number after the caustic extraction stage. A lower kappa number is desirable as it indicates that a smaller amount of lignin is present in the pulp.

The kappa number is the volume (in milliliters) of 0.1N potassium permanganate solution consumed by one gram of moisture-free pulp under the conditions specified in this Example. The results are corrected to 50% consumption of the permanganate added. The following standard method was used: TAPPI Test methods, (Tappi, Atlanta, Ga.) Vol. 1, 1988 "Kappa number of pulp—T236 cm85"). The results are shown in Table 2.

TABLE 2

| Pulp | Enzyme/Reference Treatment | | Final Brightness | Kappa number after Stage |
|---|---|---|---|---|
| | pH | T, C | % ISO | E |
| REF | 7.5 | 50 | 74.4 | 7.2 |
| | 7.5 | 70 | 74.3 | 7.2 |
| | 7.5 | 80 | 74.5 | 7.1 |
| | 8 | 70 | 74.4 | 7.2 |
| | 9 | 70 | 74.3 | 7.2 |
| | 10 | 70 | 74.3 | 7.2 |
| ENZYME TREATED | 7.5 | 70 | 79.2 | 5.2 |
| | 7.5 | 80 | 76.0 | 6.5 |
| | 7.5 | 90 | 74.7 | 7.1 |
| | 8 | 70 | 77.9 | 5.6 |
| | 9 | 70 | 76.0 | 6.5 |
| | 10 | 70 | 75.2 | 6.8 |

The results depicted in Table 2 above show that at reference pulp brightness level 74.4%, a 4.9% unit increase in the final pulp brightness is achieved by enzyme treatment at pH 7.5 and temperature 70° C. prior to chemical bleaching.

Moreover, at temperatures as high as 80° C. and alkaline pH 7.5, the oxygen delignified softwood pulp samples treated with whole supernatant xylanases derived from *Microtetraspora flexuosa* still gives a significant increase in the final pulp brightness compared to the reference pulp. Even at extreme temperatures (90° C.) and alkaline conditions (pH 7.5), whole supernatant xylanases remains active with 0.4% increase ISO units found in the treated pulp as compared to the reference pulp.

In high alkaline conditions, i.e., pH 9.0, at 70° C., significant brightening of the pulp was achieved as compared to the reference pulp. Furthermore, at extreme alkaline conditions, i.e., pH 10 at 70° C., the whole supernatant xylanases are still active with an increase of 0.9% ISO units found in the pulp compared to the reference pulp.

As it can be seen from the Kappa numbers the delignification in the extraction stage can be significantly enhanced by enzyme treatment even at alkaline pH conditions and high temperatures.

EXAMPLE 2

Enzyme treatment of oxygen delignified softwood kraft pulp prior to peroxide bleaching Oxygen delignified softwood kraft pulp, kappa number 15.7 was treated with whole supernatant xylanase enzyme derived from *Microtetraspora flexuosa* under the following conditions:

| Enzyme dosage | 10 DNS U/g pulp d.s. |
|---|---|
| pH | 7 |
| Temperature | 50° C., 60° C., 70° C. or 80° C. |
| Reaction time | 2 hours |
| Pulp consistency | 10% |

Before adding the enzyme solution into the pulp mixture, the pH of the pulp was adjusted to the value desired with sulfuric acid and the pulp mixture was preheated in a microwave oven to reach the reaction temperature required. After the pH adjustment and preheating of the pulp mixture, the enzyme was thoroughly mixed into the pulp mixture and kept 2 hours in a waterbath at the temperature desired.

After the enzyme treatment, the pulp mixture was filtered in a Buchner funnel and the pulp was washed with water. The reference pulps were treated in each pH/temperature combination as described above without adding any enzyme.

Chemical bleaching

After the enzyme or reference treatment, the pulp samples were treated with EDTA to chelate and remove metal ions harmful in the peroxide bleaching of pulp.

The reaction conditions in the chelation stage were as follows:

| EDTA | 0.2% of pulp d.s. |
|---|---|
| Temperature | 85° C. |
| pH | 4 |
| Pulp consistency | 3% |

After the chelation stage the pulps were chemically bleached by using sequence P-P. The reaction conditions used in the chemical bleaching are shown in the following table.

TABLE 3

| Bleaching stage | Reagent | % of pulp d.s. | Reaction Conditions T, °C. | t, hr | Cons., % |
|---|---|---|---|---|---|
| P1 | $H_2O_2$ | 3.5 ($H_2O_2$) pH at the end 10.5–11 | 85 | 4 | 10 |
| P2 | $H_2O_2$ | 1.5 ($H_2O_2$) pH at the end 10.5–11 | 85 | 4 | 10 |

After the chemical bleaching the pulp samples were acidified with $SO_2$ water to a pH value of 3.5 at room temperature.

The bleached pulps were analyzed for brightness (ISO) according to SCAN-C11:75. The delignification was measured as change of kappa number after stage P2. The results are shown in Table 4.

TABLE 4

| Pulp | Enzyme/Reference Treatment pH | T, C | Final Brightness % ISO | Kappa number after Stage P2 |
|---|---|---|---|---|
| REF | 7 | 50 | 76.1 | 2.9 |
|  | 7 | 60 | 76.0 | 2.9 |
|  | 7 | 70 | 76.0 | 2.9 |
|  | 7 | 80 | 75.9 | 2.9 |
| ENZYME TREATED | 7 | 50 | 76.9 | 2.7 |
|  | 7 | 60 | 77.2 | 2.7 |
|  | 7 | 70 | 78.4 | 2.6 |
|  | 7 | 80 | 76.3 | 2.8 |

The Table illustrates that a significant increase in the final pulp brightness after peroxide bleaching is achieved by treating the pulp with the whole supernatant xylanases from *Microtetraspora flexuosa* at 70° C. and pH 7 prior to the peroxide treatment compared to reference pulp. At temperatures as high as 80° C., whole supernatant xylanases remain active with 0.4% increase ISO units found in the treated pulp as compared to the reference pulp. According to the kappa numbers, delignification is clearly enhanced by enzyme treatment.

EXAMPLE 3

Enzyme treatment of oxygen delignified hardwood kraft pulp prior to D-E-D bleaching Oxygen delignified hardwood kraft pulp, kappa number 10.9 was treated with purified xylanase 1 or xylanase 2 derived from *Microtetraspora flexuosa* under the following conditions:

| Enzyme dosage | 3 DNS U/g pulp d.s. |
|---|---|
| pH | 5, 7 or 8 |
| Temperature | 70° C. or 90° C. |
| Reaction time | 2 hours |
| Pulp consistency | 10% |

Before adding the enzyme solution into the pulp mixture, the pH of the pulp was adjusted to the value desired with sulfuric acid and the pulp mixture was preheated in a microwave oven to reach the reaction temperature required. After pH adjustment and preheating of the pulp mixture, the enzyme was thoroughly mixed into the pulp mixture and kept 2 hours in a waterbath at the desired temperature.

After the enzyme treatment the pulp mixture was filtered in a Buchner funnel and the pulp was washed with water. The reference pulps were treated in each pH/temperature combination as described above without adding any enzyme.

Chemical bleaching

After the enzyme or reference treatment, the pulp samples were chemically bleached using bleaching sequence D-E-D. In both D (chlorine dioxide) stages 100% chlorine dioxide was used.

The reaction conditions used in the chemical bleaching were as follows:

TABLE 5

| Bleaching stage | Reagent % of pulp d.s. | Reaction Conditions T, C | t, min | Cons., % |
|---|---|---|---|---|
| D | 2.3 (act. $Cl_2$) | 45 | 120 | 10 |
| E | 1.2 (NaOH) | 70 | 140 | 10 |
| D | 1.0 (act. $Cl_2$) | 70 | 220 | 10 |

After the chemical bleaching the pulp samples were acidified with $SO_2$ water to pH value 3.5 at room temperature.

The bleached pulps were analyzed for brightness (ISO) according to SCAN-C11:75. The delignification was measured as a change in kappa number after stage E. The results are shown in Table 6.

TABLE 6

| Pulp | Enzyme/Reference Treatment pH | T, °C. | Final Brightness % ISO | Kappa number after Stage E |
|---|---|---|---|---|
| REF | 5 | 90 | 83.0 | 3.6 |
|  | 7 | 70 | 83.0 | 3.6 |
|  | 8 | 90 | 83.3 | 3.5 |
| XYLANASE 1 | 5 | 90 | 83.4 | 3.5 |
|  | 7 | 70 | 85.1 | 2.8 |
|  | 8 | 90 | 83.5 | 3.4 |
| XYLANASE 2 | 5 | 90 | 83.6 | 3.4 |
|  | 7 | 70 | 84.8 | 2.9 |
|  | 8 | 90 | 83.6 | 3.4 |

The results in Table 6 demonstrate the significant increase in the final pulp brightness after D-E-D bleaching achieved by treating the pulp with the purified xylanase 1 or xylanase 2 from *Microtetraspora flexuosa* at the temperature of 70° C. at pH 7 prior to the chemical bleaching. Even at temperatures as high as 90° C. and alkaline pH (pH 8.0), xylanase 2 remains active with 0.3% ISO increase as compared to the reference pulp.

Under reaction conditions pH7/70° C., delignification in stage E is clearly enhanced by enzymatic treatment. Even in extreme conditions of pH8/90° C., a reduction in the kappa number after stage E can be achieved by enzyme treatment.

EXAMPLE 4

Purification of Five Xylanases produced by *Microtetraspora flexuosa*

Xylanase Assays

The presence of xylanase was determined using a remazol brilliant blue dyed birchwood xylan (RBB-xylan) substrate (Megazyme, Australia is the commercial supplier of the substrate.) 200 ul samples are mixed with 250 ul of substrate solution (2% [w/v] RBB-xylan in 50 mM sodium citrate pH 6.5) and incubated at 37° C. for 10 minutes. Undigested xylan is precipitated by the addition of 1 ml 95% ethanol and removed by centrifugation. Released dye remaining in solution is quantified by spectrophotometry ($OD_{590}$) versus ethanol as a blank and is proportional to xylanase activity. Activity may be quantified using a standard curve and is reported as XAU/ml (xylanase activity units per milliliter).

A gel overlay method for detecting the presence of multiple xylanases and to determine their isoelectric points (pI) was also developed using RBB-xylan substrate. Isoelectric focusing (IEF) gels (pH gradient 3-9) are overlaid with a melted agarose/substrate suspension (4% [w/v] agarose, 7 mg/ml RBB-xylan, 0.5% [v/v] glycerol in 50 mM sodium citrate pH 6.5) and incubated at 37° C. After ca. 1 hour xylanase activity is evident as clearing zones. Gels are allowed to dry completely and may be stored. Xylanase pI is determined by comparison with identically run IEF gels containing silver stained pI standards.

Sample

*Microtetraspora flexuosa* ATCC 35864 fermentation broth (ca. 14 XAU/ml) was concentrated 5 X using ultrafiltration (Amicon stir-cell, 350 ml, PM-10 membrane). All samples were filter sterilized. Protein concentration was 12.5 mg/ml by a BCA method (Pierce). Gel overlay analysis determined the presence of five xylanases, pI 8.5, 7.5, 6.2, 5.8, and 5.3. These five xylanases are referred throughout the present specification as xylanases 1-5, respectively.

Purification Methods

A combination of ion exchange chromatography (IEC) and hydrophobic interaction chromatography (IEC and HIC, respectively) were used to purify all five xylanases as follows:

Purification of xylanases 1 and 2

As a first step, IEC was used to purify xylanases 1 and 2. Concentrated sample was dialyzed completely against 10 mM tris-HCl, pH 9.0 (buffer A). 50 ml were applied to a standard chromatography column (Pharmacia C 16/40) packed with 72 ml Q-Sepharose HP (Pharmacia) equilibrated with buffer A at 1 ml/min using a Pharmacia FPLC system. The column was washed with 50 ml of buffer A, then eluted with a 400 ml linear increasing salt gradient, buffer A to 0.25M NaCl in buffer A. The column was washed of remaining bound protein with 2M NaCl in buffer A. 10 ml fractions were collected and assayed as previously described.

Xylanases 1 and 2 co-eluted from the column with the initial flow through while the vast remainder of protein was bound by the column. (Xylanases 1 and 2 represent the unbound column fractions). Hydrophobic interaction chromatography (HIC) was used as a second step to purify and isolate xylanases 1 and 2. Active fractions were pooled and brought to a final ammonium sulfate concentration of 0.2M by the addition of 2M ammonium sulfate. 50 mM sodium citrate pH 6.5 was added to a final concentration of 10 mM and the material (ca. 100 ml) was applied to a standard chromatography column (Pharmacia C 16/20) packed with 36 ml Phenyl Sepharose CL-4B (Pharmacia) equilibrated with 0.2M ammonium sulphate-10 mM sodium citrate pH 6.5 (buffer B) at 0.5 ml/min. The column was washed with 60 ml buffer B, then eluted by stepping the salt concentration down to 10 mM sodium citrate pH 6.5 (buffer C) for 70 ml, stepping down to 10% (v/v) ethylene glycol (EG) in buffer C for 50 ml, applying a 200 ml linear gradient 10-32% EG, washing at 32% EG for 80 ml, applying a 150 ml gradient 32-38% EG and finally stepping up to 50% EG for 70 ml to completely wash the column. 10 ml fractions were collected and assayed as above. Under these conditions, homogeneous xylanase 2 elutes with the 32% EG wash while homogeneous xylanase 1 elutes at the tail end of the 32-38% EG gradient.

Purification of xylanase 4

Using the above described first step (IEC) for the purification of xylanases 1 and 2, xylanases 4 and 5 co-elute at ca. 0.16M NaCl in buffer A. Active fractions were pooled and brought to 0.4M ammonium sulfate-10 mM sodium citrate pH 6.5 (buffer D) as above. Material, ca. 100 ml, was applied at 1 ml/min to above described HIC column which had been equilibrated with buffer D. The column was washed with 50 ml buffer D, eluted with 130 ml linear gradient buffer D to buffer C followed immediately by a 200 ml linear gradient buffer C to 50% EG. 10 ml fractions were collected and assayed as above. Xylanase 4 elutes at ca. 20% EG.

Purification of xylanases 3 and 5

In the case of xylanases 3 and 5, HIC was used as a first step. Concentrated sample was brought to 0.5M ammonium sulfate in buffer C by the addition of 2M ammonium sulfate and 50 mM sodium citrate pH 6.5 (as above). Material was filtered to remove any trace precipitates and a 50 ml volume was applied at 1 ml/min to the above described HIC column which had been equilibrated with 0.5M ammonium sulfate in buffer C (buffer E). The column was next washed with 87.5 ml buffer E then eluted with a 147 ml linear gradient buffer E to buffer C. 10 ml fractions were collected and assayed as above. Xylanases 3 and 5 co-eluted at ca. 0.05 ammonium sulfate.

IEC was used to isolate and purify xylanases 3 and 5. Active HIC fractions were pooled (70 ml), dialyzed completely against 10 mM tris-HCl pH 8.0 (buffer F) and concentrated to ca. 20 ml by above method. Material was applied at 1 ml/min to the above described IEC column which had been equilibrated with buffer F. The column was washed with 150 ml buffer F and eluted with a 150 ml linear gradient buffer F to 0.25M NaCl in buffer F. 10 ml fractions were collected and assayed as above. Xylanase 3 eluted at ca. 0.05M NaCl while xylanase 5 eluted at ca. 0.15M NaCl.

EXAMPLE 5

Characterization of Five Xylanases produced by *Microtetraspora flexuosa*

After purification, each xylanase was subjected to isoelectric focusing and a molecular weight determination according to the following procedures. The results of the biochemical characterization of the xylanases are listed in Table 7.

Isoelectric focusing techniques were carried out using a PhastSystem (Pharmacia Biotech) as per manufacturer's instructions. Markers used for pI determination were a broad pI kit pH 3.5-9.3 (Pharmacia Biotech). Visualization of proteins was by PhastSystem development silver staining, as per instructions. Molecular weight determinations were accomplished by two methods: sodium dodecyl sulfate polyacrylamide gel electrophoresis (SDS-PAGE) and mass spectroscopy (MS). SDS-PAGE and subsequent visualization by silver staining was carried out using a Phast system, as above. Molecular weight markers used were from Sigma Chemical Co. (St. Louis, Mo.). Mass spectroscopy was performed by Charles Evans and Associates (301 Chesapeake Drive, Redwood City, Calif. 94063).

TABLE 7

Microtetra-spora flexuosa
XYLANASES

| No. | pI | MW (kD)-method | pH Optimum | pH Stability | Temperature Optimum (°C.) | Temperature Stability half-life at 80° C. (min) |
|---|---|---|---|---|---|---|
| 1 | 8.5 | 33.1-MS | 7.0–7.5 | 6–8.5 | 70 | 110 |
| 2 | 7.5 | 13.3-MS | 7.0–7.5 | 6–8 | 65 | 45 |
| 3 | 6.2 | 31.0-SDS | 7.5 | 6–9 | 65 | 30 |
| 4 | 5.8 | 50.0-SDS | 7.5 | 6–9 | 65 | 90 |
| 5 | 5.3 | 35.0-SDS | 7.5 | 6–9 | 70 | 30 |

The pH optimum is determined by using the RBB assay described previously except that the buffers vary depending on the pH ranges measured, i.e., pH 4.5–12.0. (See FIG. 1) It is within the skilled artisan's ability to prepare the appropriate buffer for the selected pH of the assay.

The temperature stability represent the time at a given temperature where half the activity remains. The activity is measured at approximately 18°–37° C. A sample is incubated at a given temperature and the activity is measured using the RBB assay. The half life is the time in minutes where half the activity is lost. (See FIG. 3)

The temperature optimum is the temperature where the highest activity is found. FIG. 2 shows the temperature profile of xylanases 1–5 measured using the RBB assay. In both FIGS. 1 and 2, the % maximum activity is related to the highest activity measurement which is given the value 100% and all other numbers are measured relative to that standardization.

All publications and patent applications mentioned in this specification are herein incorporated by reference to the same extent as of each individual publication or patent application was specifically and individually indicated to the incorporated by reference.

The invention now being fully described, it will be apparent to one of ordinary skill in the art that many changes and modifications can be made thereto without departing from the spirit or scope of the appended claims.

We claim:

1. A xylanase isolated from *Microtetraspora flexuosa* having a molecular weight of about 33,100 daltons, pI of about 8.5, an optimum pH of about 7.0 to about 7.5 and an optimum temperature activity of about 70° C.

2. A xylanase isolated from *Microtetraspora flexuosa* having a molecular weight of about 13,300 daltons, pI of about 7.5, an optimum pH of about 7.0 to about 7.5 and an optimum temperature activity of about 65° C.

3. A xylanase isolated from *Microtetraspora flexuosa* having a molecular weight of about 31,000 daltons, pI of about 6.2, an optimum pH of about 7.5 and an optimum temperature activity of about 65° C.

4. A xylanase isolated from *Microtetraspora flexuosa* having a molecular weight of about 50,000 daltons, pI of about 5.8, an optimum pH of about 7.5 and an optimum temperature activity of about 65° C.

5. A xylanase isolated from *Microtetraspora flexuosa* having a molecular weight of about 35,000 daltons, pI of about 5.3, an optimum pH of about 7.5 and an optimum temperature activity of about 70° C.

6. A method of enhancing the delignification and/or bleaching of pulp comprising contacting said pulp with one or more isolated xylanases from *Microtetraspora flexuosa* wherein said isolated xylanases are selected from the group consisting of a xylanase having a molecular weight of about 33,100 daltons, pI of about 8.5, an optimum pH of about 7.0 to about 7.5 and an optimum temperature activity of about 70° C., a xylanase having a molecular weight of about 13,300 daltons, pI of about 7.5, an optimum pH of about 7.0 to about 7.5 and an optimum temperature activity of about 65° C., a xylanase having a molecular weight of about 31,000 daltons, pI of about 6.2, an optimum pH of about 7.5 and an optimum temperature activity of about 65° C., a xylanase having a molecular weight of about 50,000 daltons, pI of about 5.8, an optimum pH of about 7.5 and an optimum temperature activity of about 65° C. and a xylanase having a molecular weight of about 35,000 daltons, pI of about 5.3, an optimum pH of about 7.5 and an optimum temperature activity of about 70° C. at a temperature, pH and xylanase concentration such that enhancement of delignification and/or bleaching is effected.

7. A method according to claim 6 wherein said isolated xylanase is the xylanase having a molecular weight of about 33,100 daltons, pI of about 8.5, an optimum pH of about 7.0 to about 7.5 and exhibits an optimum temperature activity of about 70° C.

8. A method according to claim 6 wherein said isolated xylanase is the xylanase having a molecular weight of about 13,300 daltons, pI of about 7.5, an optimum pH of about 7.0 to about 7.5 and exhibits an optimum temperature activity of about 65° C.

9. A method according to claim 6 wherein said isolated xylanase is the xylanase having a molecular weight of about 31,000 daltons, pI of about 6.2, an optimum pH of about 7.5 and exhibits an optimum temperature activity of about 65° C.

10. A method according to claim 6 wherein said isolated xylanase is the xylanase having a molecular weight of about 50,000 daltons, pI of about 5.8, an optimum pH of about 7.5 and exhibits an optimum temperature activity of about 65° C.

11. A method according to claim 6 wherein said isolated xylanase is the xylanase having a molecular weight of about 35,000 daltons, pI of about 5.3, an optimum pH of about 7.5 and exhibits an optimum temperature activity of about 70° C.

* * * * *